United States Patent
Lüscher et al.

(10) Patent No.: US 6,296,632 B1
(45) Date of Patent: Oct. 2, 2001

(54) BALL-SHAPED FIBER IMPLANT, AND METHOD AND DEVICE FOR INSERTING THE IMPLANT

(75) Inventors: Patrik Lüscher, Pfäffikon; Erich Wintermantel, Fislisbach, both of (CH)

(73) Assignee: Boston Scientific Corporation, Natick, MA (US)

( * ) Notice: Subject to any disclaimer, the term of this patent is extended or adjusted under 35 U.S.C. 154(b) by 0 days.

(21) Appl. No.: 08/776,943

(22) PCT Filed: Aug. 16, 1995

(86) PCT No.: PCT/CH95/00184

§ 371 Date: Apr. 21, 1997

§ 102(e) Date: Apr. 21, 1997

(87) PCT Pub. No.: WO96/04954

PCT Pub. Date: Feb. 22, 1996

(30) Foreign Application Priority Data

Aug. 17, 1994 (CH) .................................................. 2533/94

(51) Int. Cl.[7] ..................................................... A61K 9/22
(52) U.S. Cl. ......................... 604/890.1; 604/48; 604/502; 604/57; 604/522; 604/264; 604/93.01
(58) Field of Search ..................................... 606/108, 191, 606/192, 198, 19, 22, 35, 48, 502, 506, 518, 522, 57, 93.01, 264, 890.1, 891.1, 892.1, 1

(56) References Cited

U.S. PATENT DOCUMENTS

| Re. 34,866 | 2/1995 | Kensey et al. . |
| 903,107 | * 11/1908 | Ramus ..................................... 604/2 |
| 2,524,195 | 10/1950 | Hoover . |
| 3,431,907 | * 3/1969 | Lubet-moncla ........................ 602/45 |

(List continued on next page.)

FOREIGN PATENT DOCUMENTS

| 31 15763 | 11/1982 | (DE) . |
| 0186632 | 7/1986 | (EP) . |
| 0 621 020 | 10/1994 | (EP) . |

(List continued on next page.)

OTHER PUBLICATIONS

Ayumi, Igaku No. [SIC], "Situtation of New Subspeciality of Neurosurgery"; vol. 154, No. 7, p. 432, Aug. 1990, Ishiyaku Publishers, Inc.

Goto, K., "Recent Advances and Future Problems of Interventional Neuroradiology"; Neurosurgeons 9:229–239, Sep. 1990.

Taki, K., "Possibility and Limit of Intravascular Surgery"; Medical Tribune, pp. 46–47, Oct. 1989, Nippon Accel Shubringer Shuppan, K. K.

(List continued on next page.)

Primary Examiner—Glenn K. Dawson
(74) Attorney, Agent, or Firm—Finnegan, Henderson, Farabow, Garrett & Dunner, L.L.P.

(57) ABSTRACT

In the method proposed, the implant material in the form of a fibre is unwound from a bobbin (10) with the aid of a stream of air (24) and injected through a tube (19) into the body (22). In front of the distal opening (20) of the fibre injection tube, the implant material forms a coherent, open-pore structure in the form of a ball of fibre (25). The fibre-injection tube (19) can be a syringe needle, a catheter or an endoscope tube. This enables the implant (25) to be inserted using minimum-invasive surgery. The size and shape of the implant thus produced can be very variable and can be determined intra-operatively. Various implant materials and fibre shapes can be used. Possible applications of the implant are in the filling of body cavities, systems for the controlled release of systemically acting drugs or chemotherapeutic agents, the induction of tissue, cell transplantation and therapeutic embolization.

25 Claims, 3 Drawing Sheets

U.S. PATENT DOCUMENTS

| | | | |
|---|---|---|---|
| 3,481,335 | * 12/1969 | Beutlich | 604/11 |
| 3,703,174 | 11/1972 | Smith . | |
| 3,826,256 | 7/1974 | Smith . | |
| 3,906,550 | 9/1975 | Rostoker et al. . | |
| 4,159,022 | 6/1979 | Pevsner . | |
| 4,237,885 | 12/1980 | Wong et al. . | |
| 4,402,308 | 9/1983 | Scott . | |
| 4,512,338 | 4/1985 | Balko et al. . | |
| 4,551,132 | 11/1985 | Pasztor et al. . | |
| 4,820,767 | 4/1989 | Wu . | |
| 4,840,622 | 6/1989 | Hardy . | |
| 4,932,942 | 6/1990 | Maslanka . | |
| 4,950,295 | 8/1990 | Weigum et al. . | |
| 4,994,069 | 2/1991 | Ritchart et al. . | |
| 5,021,059 | 6/1991 | Kensey et al. . | |
| 5,074,840 | * 12/1991 | Yoon | 604/11 |
| 5,100,392 | 3/1992 | Orth et al. . | |
| 5,211,627 | 5/1993 | William . | |
| 5,250,071 | * 10/1993 | Palermo | 606/198 |
| 5,256,146 | * 10/1993 | Ensminger et al. | 606/198 |
| 5,263,927 | * 11/1993 | Shlain | 604/13 |
| 5,308,342 | 5/1994 | Sepetka et al. . | |
| 5,318,524 | 6/1994 | Morse et al. . | |
| 5,322,510 | 6/1994 | Lindner et al. . | |
| 5,336,263 | 8/1994 | Ersek et al. . | |
| 5,374,261 | 12/1994 | Yoon . | |
| 5,376,118 | * 12/1994 | Kaplan et al. | 606/230 |
| 5,443,454 | 8/1995 | Tanabe et al. . | |
| 5,454,833 | 10/1995 | Boussignac et al. . | |
| 5,514,158 | 5/1996 | Kanesaka . | |
| 5,522,795 | * 6/1996 | Green et al. | 604/11 |
| 5,522,822 | * 6/1996 | Phelps et al. | 606/151 |
| 5,545,169 | * 8/1996 | Yarger | 606/108 |
| 5,571,189 | 11/1996 | Kuslich . | |
| 5,575,815 | 11/1996 | Slepian et al. . | |
| 5,591,224 | 1/1997 | Schwartz et al. . | |
| 5,614,204 | 3/1997 | Cochrum . | |
| 5,660,854 | * 8/1997 | Haynes et al. | 606/231 |
| 5,667,778 | 9/1997 | Atala . | |
| 5,766,160 | 6/1998 | Samson et al. . | |
| 5,954,682 | * 9/1999 | Petrus | 604/11 |

FOREIGN PATENT DOCUMENTS

| | | |
|---|---|---|
| 2 696 636 | 4/1994 | (FR) . |
| 61-161220 | 7/1986 | (JP) . |
| 2-280768 | 11/1990 | (JP) . |
| 2-280769 | 11/1990 | (JP) . |
| 2-280770 | 11/1990 | (JP) . |
| 2-280771 | 11/1990 | (JP) . |
| 4-20348 | 1/1992 | (JP) . |
| 4-197359 | 7/1992 | (JP) . |
| 5-208917 | 8/1993 | (JP) . |
| WO 91/13592 | 9/1991 | (WO) . |
| WO 93/00127 | 1/1993 | (WO) . |
| 5-504695 | 7/1993 | (WO) . |
| WO 94/16632 | 8/1994 | (WO) . |
| WO 97/19643 | 6/1997 | (WO) . |

OTHER PUBLICATIONS

Bernatchez et al., "Biocompatibility of a New Semisolid Bioerodible Poly(ortho ester) Intended for the Ocular Delivery of 5–fluorouracil"; Journal of Biomedical Materials Research; vol. 28, No. 9, pp. 1037–1046, Sep. 1994.

Bernatchez et al., "Biotolerance of a Semisolid Hydrophobic Biodegradable Poly(ortho ester) for Controlled Drug Delivery"; Journal of Biomedical Materials Research; vol. 27, No. 5, pp. 677–681, May, 1993.

Taki et al., "The Eleventh General Meeting of Japan Biomaterial Society Collection of Scripts for Presentation"; Oct. 1989, At Kyoto University, Chief of the 11th Meeting: Takao Yamamuro.

Ayumi, Igaku No. [SIC], "Embolization Technique of Cerebral Arterial Aneurysm Advantages and Disadvantages of Embolization Technique and Surgical Operation"; vol. 153, No. 11, p. 635, Jun. 1990, Ishiyaku Publishers, Inc.

Goto, K., et al., "A New Technique for Embolization of Cerebral Arteriovenous Malformations and Dural Arteriovenous Fistulae"; Neuroradiology (1991) 33[Suppl] :193–194.

Harper, Marion, et al., "Isobutyl 2–cyanoacrylate as an Osseous Adhesive in the Repair of Osteochondral Fractures"; Journal of Biomedical Materials Research, vol. 17, pp. 167–177 (1983).

Serbinenko, F.A., M.D., "Balloon Catheterization and Occlusion of Major Cerebral Vessels"; J. Neurosurg, vol. 41, Aug. 1974, pp. 125–145.

Rüfenacht, D.A. et al., "A Simple Propulsion–Chamber–System for the 16 Gauge Approach"; Neuroradiology (1986) 28:355–358.

Marks, R., et. al., "Principles of Weaving"; The Textile Institute Manchester, 1976, pp. 130–135.

A. Polk et al., "Controlled Release of Albumin from Chitsan–Alginate Microcapsules," Journal of Pharmaceutical Sciences, vol. 83, No. 2 (Feb. 1994), pp. 178–185.

K. Kamath et al., "Biodegradable Hydrogels in Drug Delivery," Advanced Drug Delivery Reviews, 11 (1993), pp. 59–84.

* cited by examiner

BALL-SHAPED FIBER IMPLANT, AND METHOD AND DEVICE FOR INSERTING THE IMPLANT

FIELD OF THE INVENTION

This invention is regarding an implant, the usage of this implant, as well as the device and the method for the application of the implant.

BACKGROUND OF THE INVENTION

In medicine, implants are known for their different uses, and their numerous types. In general, implants are inserted in their entirety which involves a comparatively large surgical operation thus resulting in a corresponding high strain on the patient.

SUMMARY OF THE INVENTION

The basic task of this invention is to create an implant which can be used while exerting minimal strain on the patient and which is distinguished by its vast range of application. With the same purpose, the task of this invention is to create a device for the application of the implant as well as to create a method for the application of the implant.

According to this invention, the implant is characterized by a ball of fiber which is in the form of a three-dimensional, open-pore structure. Such a ball of fiber can be introduced, in optional amounts (in situ) via a small insertion using surgical micro-technology with minimal strain to the patient. A wide variety of possible applications arise particularly from the fact that the size and the shape of the implant are widely variable and can be determined during the operation. For example, the pore-size and the structural characteristics of the implant can be varied by modifying the material characteristics, in particular the fiber. The fiber can be the carrier of biologically active substances and is particularly suitable for controlled medication-release or for the induction of body-tissue. Numerous applications are also envisioned for the fields of dentistry and veterinary medicine.

According to this invention, the device for the application of the implant is characterized by a tube and instruments, which deliver the implant in fiber-shaped form through a distal opening of the tube. Since the device, (according to this invention), leads the implant in fiber-shaped form through the tube and deposits it at this point, an application using surgical micro technology and hence a minimal invasive implantation is possible.

According to a further development of the device, (according to this invention), a fluid-stream is generated by the aforementioned instruments, with which the fiber can be transported through the tube. In addition, the fluid together with the fiber can be delivered through the distal opening of the tube. The fluid, for example, can be designed to serve as a carrier of biologically active substances or as an adhesive for the local stabilization of the fiber which has been deposited within the tissue. Another model is also conceivable, in which the fluid is carried off via an intake-tube which reverses the fluid. The fluid can be a liquid, a suspension, in particular autologous blood, or an electrolyte solution, but also a gas.

According to this invention, this method is characterized by the fact that the implant is brought in fiber-shaped form to the application site, where it is deposited as a three dimensional ball of fiber. This method makes possible the introduction of an implant via an existing or a created small body opening. Therefore this method is possible with minimal strain to the patient. Nevertheless the implant, in its fully developed form, can be a large volume. For example in orthopedic cases, the fiber ball can fill a relatively large tissue defect, in particular a bone defect. The attending physician can precisely determine the length of the fiber and then, for example, measure precisely the administration of medication.

According to a further development of the method, (according to this invention), the fiber is inserted in such away that an end of the fiber protrudes from the insertion site or body-opening respectively. Such an implant can be explanted very easily at any time, in that the fiber is grasped at the protruding end and extracted from the insertion site.

Other characteristics and advantages become apparent from the associated patent claims, the description, as well as the figures. Application examples of the invention are explained subsequently using the figures. It is shown:

DETAILED DESCRIPTION OF THE INVENTION

Figure 1:
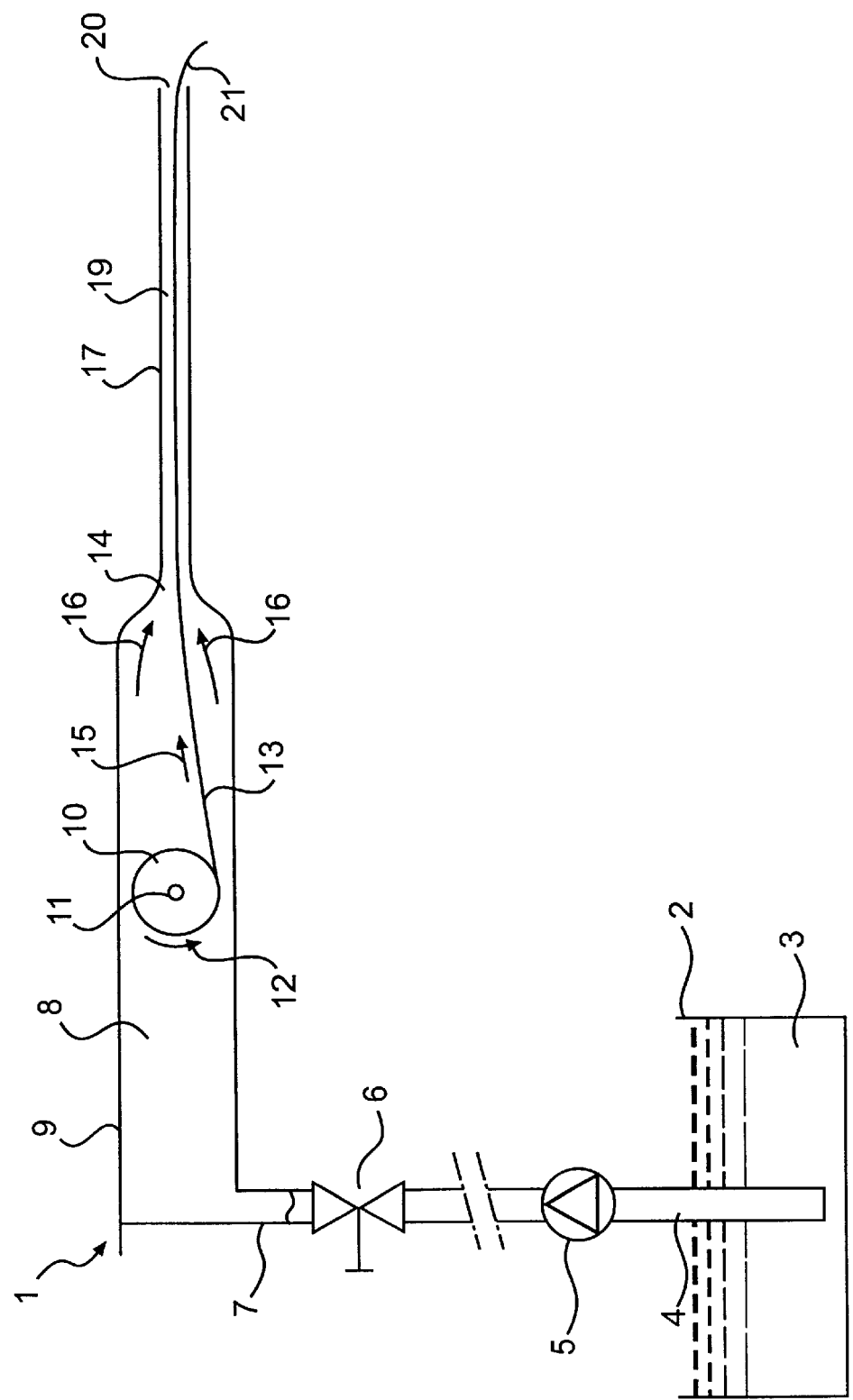
FIG. 1 schematically, a cross-sectional view of a device, (according to this invention), FIGS. 2 and 3 schematically, the application of an implant, (according to this invention), FIG. 4 an implant inserted into tissue FIG. 5 schematically, a cross-sectional view of a variation of the device, (according to this invention)

According to this invention, the device (1) exhibits (according to FIG. 1) a casing (9), which has an interior volume (8) leading into the tube (19) of a hollow needle (17), and which is also connected to tubing (7) through which a fluid (3), in particular a liquid, can be delivered from a container (2) to the interior volume (8). The fluid (3) is delivered by means of a suction pipe (4) and a pump (5) into the tubing (7), in which a valve (6) is used for the dosage of the fluid stream.

Inside of the interior volume (8) a fiber bobbin (10) is affixed to an encased axle (11) in such a way that it turns in the direction of the arrow (12). The bobbin (10) is arranged in such a way, that a fiber, which is wound up on it, can be unwound in direction of the arrow (15) into the tube (19) of the hollow needle (17). Hereby, the fiber (13) is inserted into a proximal opening (14) of the tube (19) and leaves the tube through a distal opening (20). Another type is also conceivable, according to which the bobbin (10) is affixed outside of the casing (9). Further types are conceivable, in which the bobbin (10) is substituted by another suitable supply device. Finally, types are conceivable, in which the fiber (13) is shorter, or not significantly longer than the tube (19), so that a bobbin (10) or suchlike is not required. The tube (19) is designed is such a way, that the fiber (13) can glide within the tube (19) without any significant friction. In addition, fluid streams from the interior volume (8) in the direction of the arrow (16) into the proximal opening (14) and into the tube (19), where it flows through the tube (19) thereby transporting the fiber (13). The speed of the transport of the fiber (13) in the tube (19) can be increased in particular through the increase of the fluid pressure in the chamber (8). The transport of the fiber can be suspended with an interruption of the fluid-stream at the valve (6). Finally it is possible, that the entire piece of fiber can be delivered to the outside through the distal opening (20).

Figure 3:
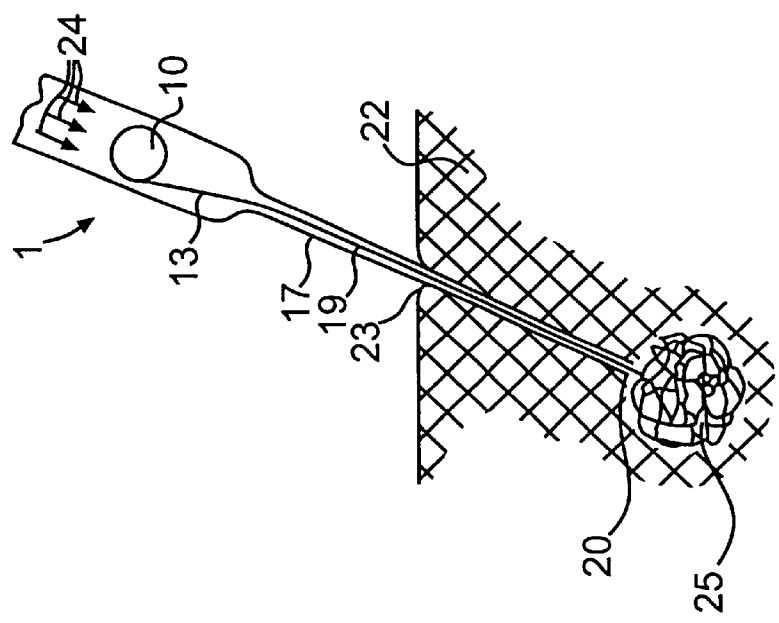
Figure 2:
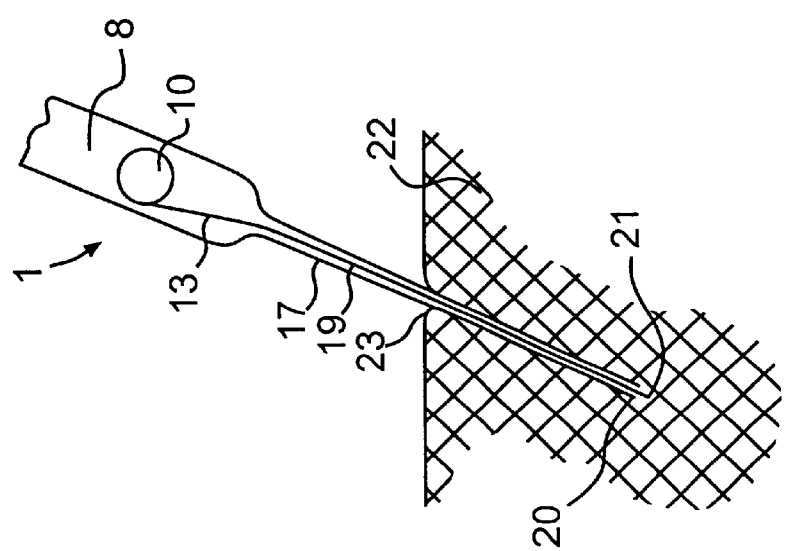

The tube (19) of the hollow needle (17) is designed in such a way that its distal opening (20), (according to FIG. 2), can be pushed through an insertion-opening (23) to a desired site in the tissue (22) or to any other site of the patient's body. When, by adjusting the valve (6), fluid (3) is introduced into the interior volume of this precisely positioned device (1), then this fluid streams in the direction of the arrow (24) (FIG. 3) towards the proximal opening (14) of the tube (19) and into the tube (19). The fiber is unwinding from the bobbin (10), as the fluid transports the fiber (13) towards the distal opening (20) and finally to the outside. The end (21) of the fiber (13), which emerges from the distal opening (20), experiences resistance once it is within the tissue (22). Consequently the following fiber sections are bent and are finally deposited in a ball of fiber (25), (as FIG. 3 demonstrates). Hereby it is essential, that the fiber (13) is lead into the tube (19) near to the opening (20) and can be pushed to the outside.

In this case the fiber (13) is understood to be an interconnected structure with an essentially round cross section, which is very small in relation to its length. The fiber can also be a hollow fiber and/or porous, which means that the fiber is permeable from the inside to the outside, and contains a medication. Particularly suitable materials are inorganic gels, for example materials on a silicon-oxide base or calcium-phosphate base, or gels made of synthetic or natural polymers, for example poly-lactid gel or calcium-alginate gel. Suitable are also synthetic polymers, for example polyorthoester, or natural polymers, for example collagen or heparin. Other applications are conceivable, in which a fiber made of autologous blood components, for example a fibrin-thrombocytes fiber, a fiber made of reabsorbable ceramic fibers, for example a calcium-phosphate fiber, a metal fiber, or a composite fiber made of several materials are particularly suitable.

The fiber (13) is designed in such a way, that the fiber is, as described above, pliable and foldable. Preferably the fiber exhibits the same diameter throughout its entire length. Yet it is also conceivable that the diameter changes regularly or irregularly along the fiber.

Preferably the fiber (13) together with the fluid (3) is discharged at the distal opening, so that the ball (25) is surrounded by injected fluid. In the case of a ball (25), which is shaped in such a way, the fiber and the fluid (3) can be both carriers of biologically active substances or particles, for example cells. However the fluid (3) can also be an adhesive, for example a fibrin adhesive, which stabilizes the structure of the ball (25).

By choosing a suitable fiber and fluid, the characteristics of the ball (25) are thus very variable. Furthermore, the size and the structure of the ball (25) can be varied by the length of the fiber and the application technique. Therefore, the form and the size of the ball of fiber (25) can be largely determined during the operation. The size of the pores as well as the structural characteristics of the ball (25) can also be manipulated to a large extent. The choice of the material characteristics of the fiber (13), the fluid (3), as well as the application technique makes this particularly feasible.

The fluid (3) can be a liquid or a gas. If a gas is selected for the fluid (3), the container has to be accordingly designed as a gas container. In this case a pump (5) is generally not necessary. The choice of the fluid (3) is determined by the intended application. Autologous blood, autologous serum or blood fractions, as well as electrolyte solution are particularly suitable as fluids (3). If the fluid (3) is supposed to stabilize the ball (25), a fibrin adhesive, which can be made of blood, is particularly suitable. A suspension, for example a bone powder or micro spheres or cell suspension, for example bone marrow cells, can serve as the fluid (3) in the case of tissue induction. If the fluid (3) is a gas, then nitrogen is particularly suitable.

The preceding explanations should clarified that the implant, according to this invention, possesses a wide scope of application within medicine as well as within veterinary medicine. In the following several advantageous application possibilities will be discussed.

An essential application of the implant (25), (according to this invention), is the induction of body tissue in cases of tissue engineering. The fiber (13) and/or the fluid (3) can be carriers of cells or cell suspension, which after the formation of the ball of fiber (25) develop new tissue or induce the generation of tissue. The generation of bone tissue in cases of bone defects or in cases of gaps between endoprosthesis and bones is particularly envisioned. Likewise, the implantation of a ball (25) can induce bone tissue in cases of vertebra- or joint-fusion, or dentistry. Further applications of the tissue induction are the induction of callus in a case of a bone fracture, as well as tissue induction in plastic surgery, for example induction of connective tissue, cartilage tissue, or endothelium.

Apart from the aforementioned applications for tissue induction, the release of systematically acting medicine or locally acting substances is also possible. Locally acting medications are in particular antibiotics or cytotoxines for the treatment of cancer. According to this invention the implant distinguishes itself particularly by the fine measurability of the acting substances. Even very small amounts of the substance can be precisely determined by choosing the length of the fiber (13). In addition the release kinetics can be determined by choosing the density of the ball (25). A dense ball (25) can dispense an acting substance more slowly than a loose ball (25). In addition a multi-level release of active agents is possible.

The fiber (13) can also function as a cell carrier, for example a carrier for encysted xenogeneic cells, for example Langerhans cells, nerve cells, or genetically altered cells.

According to this invention a further application for the implant is the therapeutic embolization of, for example hemangioma. Hereby the fiber is inserted into the central vessel of the hemangioma. The very strongly thrombogenic ball of fiber (25) clogs the blood supply of the hemangioma.

A further application for the implant, (according to this invention), is the controlled application of active agents on mucous membranes. For this purpose, a fiber which clings to mucous membranes is brought onto the mucous membranes with the device, (according to this invention), where it releases active agents, which are contained within the fiber, into the mucous membranes.

Therefore according to this invention the implant, in the essential applications, is not "carrying weight" and metabolically inductive.

Figure 4:
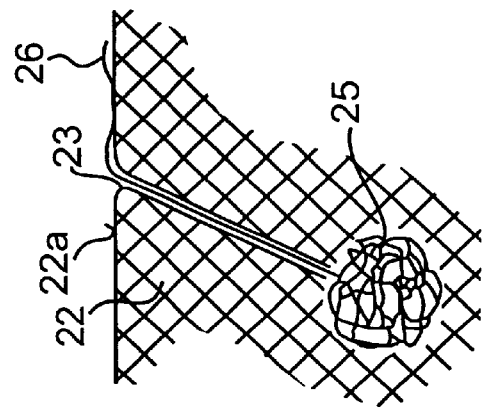

The fiber (13) can be delivered into the tissue (23) in such a way, that the fiber lies completely within the tissue. However if an explantation of the ball of fiber (25) or an injection or an infusion of medication is intended, then it becomes necessary to position the posterior end (26) of the fiber (13) (according to FIG. 4) in such a way that it protrudes from the puncture site (23). For example the end (26) can be affixed with a piece of adhesive tape (not shown here) on the outer site of the tissue (22a). In the case of an explantation, the fiber (13) is extracted from its end (26) out of the tissue (22). A surgical operation, which would be detrimental to the patient, is hereby not necessary.

Figure 5:
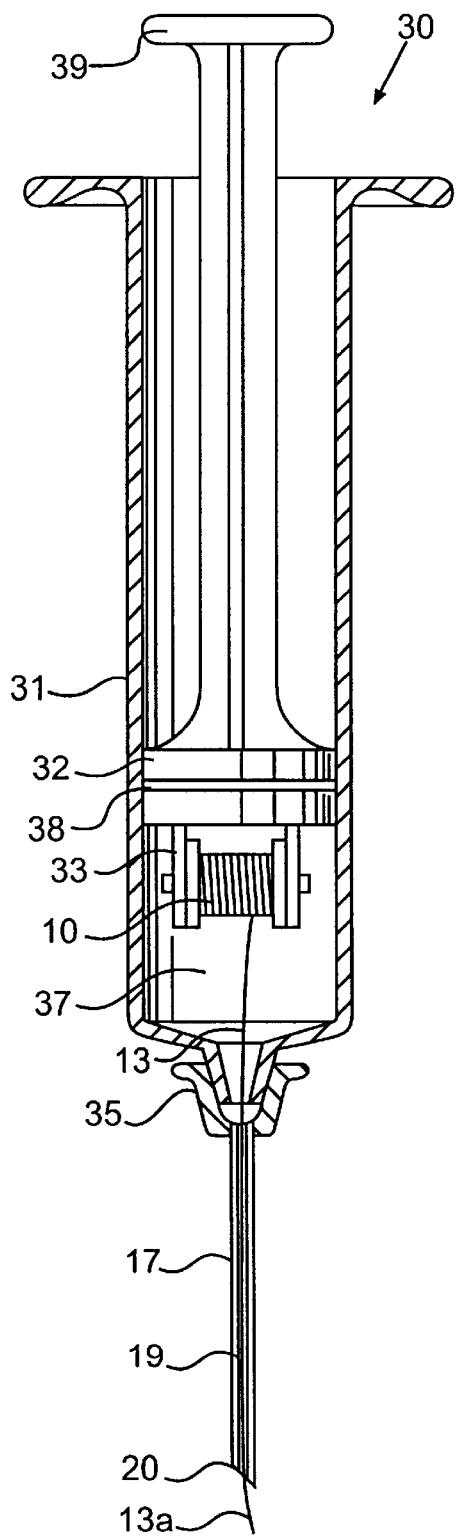

According to the type shown in FIG. 5, the device for the application of the implant is designed as a syringe (30). In particular this is a disposable syringe which is characterized by a casing (31) and a plunger (32) with a gasket (38). The plunger (32) can be moved with a grip (39) within the casing in the usual way. A mounting (33) for the bobbin of fiber (10), on which the fiber (13) is wound on, is positioned on the anterior end of the plunger. Before using the syringe (30), the anterior end (13a) of the fiber (13) should be preferably inserted at least partially into the tube (19) of the hollow needle (17). The hollow needle can be designed like a usual cannula, and is equipped with a snap-on part (35). The hollow space (37) of the syringe (30) contains an aforementioned fluid. When the plunger (32), (lay-out according to FIG. 5), is moved towards the left, the fluid streams under the appropriate pressure into the tube (19), thereby moving along the fiber (13), which has been previously inserted into the tube (19), and unwinding it from a rotating bobbin. The implant is formed within the tissue at the distal end of the hollow needle, as described above.

Other models are also conceivable in which no fluid is used for transporting the fiber (13) through the tube (19). For example the means for the transport can be a propelled bobbin (not shown here) which is positioned at the distal end of the hollow needle (17) and moves the fiber.

Figure 6:
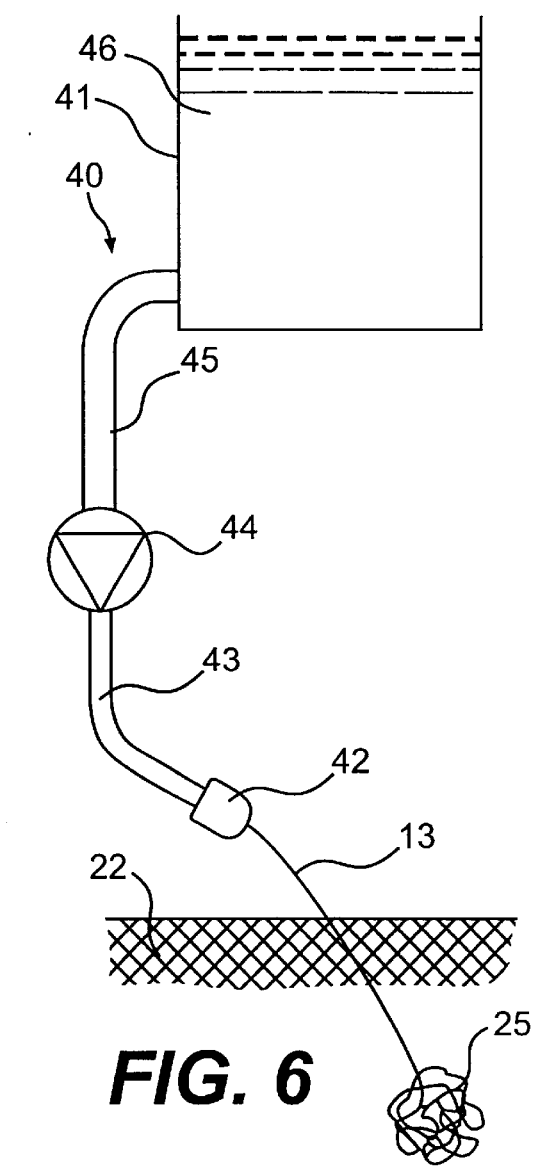
FIG. 6 schematically, an implant with a connected injector.
Figure 7:
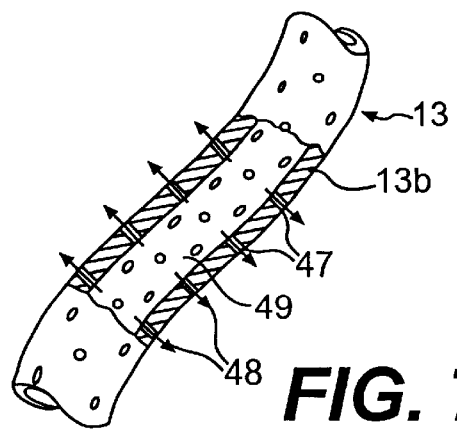
FIG. 7 a section of the fiber in an enlarged scale.

Once an implant (25) has been applied within a tissue, an injector (40) can be connected with an adapter (42) to a protruding end of the fiber (13) (according to FIG. 6). The injector (40) exhibits a reservoir (41) with an active agent (46), a suction tube (45), a pump (44), as well as an inlet tube (43). When the pump (44) is running, an active agent, in particular medication, is lead from the reservoir to the fiber (13). If the fiber (13), (according to FIG. 7), is a hollow fiber with passage openings (47) or pores, hence permeable from the inside to the outside, then the active agent (46) that reaches the hollow space (49) (FIG. 7) of the fiber, can be released through the wall (13b) in the direction of the arrows (48) into the tissue (22) or a body opening. Thereby a precisely measured and directed release of the active agent can be achieved. Likewise in this case the implant can be removed after the treatment.

What is claimed is:

1. An implant comprising:
    an elongate fiber bent in a plurality of locations along the length thereof to form a generally ball shaped structure, the fiber of the ball shaped structure being unbiased such that each of the bends in the ball shaped fiber can be formed as movement of the fiber is resisted,
    wherein the fiber includes a hollow portion containing a drug capable of being released after the fiber is implanted in a body.
2. The implant of claim 1, wherein the fiber is porous and wherein the drug is released in a controlled manner through pores in the fiber when the fiber is implanted in the body.
3. The implant of claim 1, wherein the fiber is bent so that open pores are formed in the generally ball shaped structure between portions of the fiber spaced from one another.
4. The implant of claim 1, wherein the fiber includes an end portion extending from the generally ball shaped structure, the end portion having a length sufficient to be located outside of the body when the generally ball shaped structure is implanted in the body.
5. The implant of claim 1, wherein the fiber is formed of a polymer.
6. The implant of claim 1, wherein the fiber is formed of a biologically degradable material.
7. The implant of claim 1, wherein the fiber carries one of cells and a cell suspension capable of being released when the fiber is implanted in the body.
8. The implant of claim 1, wherein the fiber is formed of a pliable material so that the fiber bends to form the generally ball shaped structure when the fiber contacts body tissue.
9. The implant of claim 1, wherein the fiber is formed of a material including alginate.
10. The implant of claim 1, wherein the fiber carries one of cells and a cell suspension capable of being released when the fiber is implanted in a body.
11. An implant comprising:
    an elongate fiber bent in a plurality of locations along the length thereof to form a generally ball shaped structure, the fiber being formed of a material including alginate, the fiber of the ball shaped structure being unbiased such that each of the bends in the ball shaped fiber can be formed as movement of the fiber is resisted.
12. The implant of claim 11, wherein the fiber is bent so that open pores are formed in the generally ball shaped structure between portions of the fiber spaced from one another.
13. The implant of claim 11, wherein the fiber includes an end portion extending from the generally ball shaped structure, the end portion having a length sufficient to be located outside of a body when the generally ball shaped structure is implanted in the body.
14. The implant of claim 11, wherein the fiber includes a drug capable of being released when the fiber is implanted in a body.
15. The implant of claim 11, wherein the fiber is porous.
16. The implant of claim 11, wherein the fiber is formed of a polymer.
17. The implant of claim 11, wherein the fiber is formed of a biologically degradable material.
18. The implant of claim 11, wherein the fiber carries one of cells and a cell suspension capable of being released when the fiber is implanted in a body.
19. The implant of claim 11, wherein the material also includes calcium.
20. The implant of claim 11, wherein the fiber includes an agent for promoting tissue growth, the agent being capable of being released when the fiber is implanted in a body.
21. The implant of claim 11, wherein the fiber is formed of a pliable material so that the fiber bends to form the generally ball shaped structure when the fiber contacts body tissue.
22. The implant of claim 11, wherein the fiber includes a medication capable of being released when the fiber is implanted in a body.
23. The implant of claim 11, wherein the fiber includes a biologically active substance capable of being released when the fiber is implanted in a body.
24. A system comprising:
    an implant comprising an elongate fiber bent in a plurality of locations along the length thereof to form a generally ball shaped structure, the fiber of the ball shaped structure being unbiased such that each of the bends in the ball shaped fiber can be formed as movement of the fiber is resisted; and
    a fluid at least partially surrounding the generally ball shaped structure, the fluid including a biologically active substance,
    wherein the fiber is formed of a material including alginate.
25. An implant comprising:
    an elongate fiber bent in a plurality of locations along the length thereof to form a generally ball shaped structure, wherein the generally ball shaped structure is at least partially surrounded by an adhesive for stabilizing the generally ball shaped structure, and wherein the fiber is formed of a material including alginate.

* * * * *

UNITED STATES PATENT AND TRADEMARK OFFICE
CERTIFICATE OF CORRECTION

PATENT NO.    : 6,296,632 B1
DATED         : October 2, 2001
INVENTOR(S)   : Patrik Lüscher et al.

It is certified that error appears in the above-identified patent and that said Letters Patent is hereby corrected as shown below:

<u>Title page,</u>
Item [57], delete the ABSTRACT and insert the following in place thereof:

--  A ball-shaped implant made out of a pliable fiber. The fiber is introduced into the body and when it encounters body tissue it folds upon itself to form a ball-shaped implant. A fluid may be placed around the implant either to hold it in place or to add a biologically active agent to the implant. The fiber of the implant may be biodegradable, or hollow and porous to allow for drugs placed inside the fiber to be administered to the body. One end of the fiber may be long enough to extend out of the body for later removal. --

Signed and Sealed this

Eleventh Day of June, 2002

*Attest:*

JAMES E. ROGAN
*Attesting Officer*     *Director of the United States Patent and Trademark Office*